United States Patent [19]
Hori et al.

[11] Patent Number: 5,348,394
[45] Date of Patent: Sep. 20, 1994

[54] METHOD AND APPARATUS FOR MEASURING FLUID THERMAL CONDUCTIVITY

[75] Inventors: Tomoshige Hori, Kitamoto; Yasuhiko Shiinoki, Tokyo; Kensuke Ito, Kodaira, all of Japan

[73] Assignee: Snow Brand Milk Products Co., Ltd., Hokkaido, Japan

[21] Appl. No.: 78,833

[22] Filed: Jun. 21, 1993

[30] Foreign Application Priority Data

Jun. 22, 1992 [JP] Japan .................. 4-187531
Sep. 24, 1992 [JP] Japan .................. 4-279340

[51] Int. Cl.$^5$ .................. G01N 25/18; G01K 1/14
[52] U.S. Cl. .................. 374/44; 374/164
[58] Field of Search .................. 374/44, 164, 208

[56] References Cited

U.S. PATENT DOCUMENTS

| | | | |
|---|---|---|---|
| 2,475,138 | 7/1949 | Hood, Jr. et al. | 374/44 |
| 3,672,205 | 6/1972 | Leidenfrost | 374/44 |
| 4,232,543 | 11/1980 | Eguchi et al. | 374/44 |

FOREIGN PATENT DOCUMENTS

| | | | |
|---|---|---|---|
| 404178550 | 6/1992 | Japan | 374/44 |
| 0879423 | 11/1981 | U.S.S.R. | 374/44 |
| 1062587 | 12/1983 | U.S.S.R. | 374/44 |
| 2170317 | 7/1986 | United Kingdom | 374/44 |

*Primary Examiner*—Diego F. F. Gutierrez
*Attorney, Agent, or Firm*—Griffin Butler Whisenhunt & Kurtossy

[57] ABSTRACT

A heating sensor is disposed within a pipe with a clearance between an inner wall of the pipe and an outer surface of the heating sensor such that a measurement of thermal conductivity is free from any influence of a convective heat transfer. Temperatures of the fluid and the heating sensor are measured and a differential temperature therebetween in steady state heating is determined. A correlation is established between the differential temperature and a thermal conductivity of the fluid and is utilized to obtain the thermal conductivity of this fluid.

11 Claims, 13 Drawing Sheets

METHOD AND APPARATUS FOR MEASURING FLUID THERMAL CONDUCTIVITY

BACKGROUND OF THE INVENTION

The present invention relates to method and apparatus for measurement of fluid thermal conductivity utilizing a steady state hot-wire method, wherein thermal conductivity of fluids being tested are obtained on the basis of a differential temperature between an electrically heating sensor arranged in thermal contact with the fluids to be measured and the fluids during heat generation from the heating sensor.

In general, the thermal conductivity of potential process fluids such as liquid mixture of liquid and solids or gas is one of the most important factors to be properly monitored and/or controlled throughout the production facilities in various industries since the thermal conductivity of a fluid largely depends on temperature, composition, mixing condition of ingredients and other factors. Furthermore it is essentially to measure the thermal conductivity directly on the production facilities in view of the fact that the thermal conductivity is one of the physical properties that is unpredictable from known additive properties. Particularly in a process involving an operation of heating and/or cooling, the optimal control conditions for such heating and/or cooling will vary and, in consequence, significantly affect the product quality as a change occurs in the thermal conductivity. Accordingly, it is essential for the process control to measure the thermal conductivity and thereby to correspondingly change the condition of control.

Additionally, if the concentration of a composition of substances such as emulsion can be determined on the basis of a change in the thermal conductivity, the in-line control of said concentration will be drastically facilitated and therefore the thermal conductivity will be one of the most important factors to be measured in such case.

Practice in the measurement of the fluid thermal conductivity by the unsteady state hot-wire method is well known, for example, from the following literature:

1. U. Nagasaka and A. Nagashima: "Study on Measurement of Fluid Thermal Conductivity with High Precision," Transactions of the Japan Society of Mechanical Engineers, Vol. 47, 417 (May, 1981), pp. 821-829;

2. U. Nagasaka and A. Nagashima: "Study on Measurement of Fluid Thermal Conductivity with High precision", Transactions of the Japan Society of Mechanical Engineers, Vol. 47, 419 (July, 1981), pp. 1323-1331; and 3. "Handbook of Thermophysical Properties", edited by Japanese Society of Thermophysical Properties, May 30, 1990, published from YOKENDO, pp. 568-573

The method for measurement of fluid thermal conductivity is generally classified into the unsteady state hot-wire method and the steady stale hot-wire method.

The unsteady state hot-wire method utilizes a time-depending change appearing in a temperature of the heating element in unsteady state in which the temperature rises as time passes, starting immediately from the initiation of heat generation to determine a thermal conductivity of the fluid to be measured. The steady state hot-wire method, on the other hand, utilizes a steady state temperature field, i.e., performs the measurement at a time-independent constant temperature reached after said unsteady state has been stabilized.

In general, the steady state hot-wire method is apt to be affected by a convective heat transfer due to convection caused by a temperature rise of the fluid to be measured and it will be impossible to determine the thermal conductivity with high precision unless the affect of the convection is eliminated. In contrast with the steady state hot-wire method, the unsteady state hot-wire method is advantageous in that the adverse effect of the convection can be reliably eliminated by detecting the onset of the convection and utilizing the value obtained prior to said generation of the convection.

This is why the unsteady state hot-wire method has been often employed in practice to measure a thermal conductivity of fluid.

Both above-identified literature references 1 and 2 report typical embodiments of the unsteady state hot-wire method, for example, a metallic thin wire placed in sample fluid in a vertical orientation is energized and a thermal conductivity is calculated based on the heating value and the temperature of the filament thus energized. Literature reference 3 describes details of both the steady state hot-wire method and the unsteady state hot-wire method.

The present invention is relevant particularly to a so-called concentric cylinder method as an embodiment of the steady state hot-wire method as described in the literature reference 3. With this concentric cylinder method, fluid to be measured is introduced into the clearance defined between an outer and an inner cylinders and the temperature of the fluid in the clearance is measured by a plurality of thermocouples while a heating element contained within the inner cylinder along a central axis thereof is energized for heat generation.

The unsteady state hot-wire method for measurement of fluid thermal conductivity as described in the above-identified literature uses platinum thin wire whose diameter is less than 50 microns in order to improve the precision of the measurement. Accordingly, actual operation of the measurement is conducted on separately provided samples of fluid and cannot be used for in-line measurement within a plant. This is true also with respect to the steady state hot-wire method described in literature reference 3.

In other words, no attempt has been made to realize an in-line measurement of the fluid thermal conductivity on actual site of production.

For measurement of the thermal conductivity using the steady state hot-wire method, a convection heat transfer possibly occurring in the fluid around the heating element must be reliably avoided. Otherwise, undesirable heat movement would be caused by a convective heat transfer, resulting in a value of the measured thermal conductivity substantially higher than an apparent effective thermal conductivity calculated on the basis of a heat movement caused only by conductive heat transfer in a static state of the fluid.

The above-identified literature references exemplarily report the method of measurement in which the fluid to be measured is confined in a clearance defined between the heating element and a spacer means. However, such method neither assumes a convection of the fluid possibly occurring in the clearance nor considers an influence of such convection on the measurement. Further, such an apparatus used to perform such method is too complicated to be incorporated in a production line, and even if such incorporation is possible, would inevitably encounter a problem such as washability.

The typical apparatus with tile concentric cylinder method that is conventionally known has been disadvantageously complicated and expensive since the apparatus comprises a plurality of thermometers contained within a cell particularly made of silver to achieve a uniform temperature distribution of the sampled fluid.

Japanese patent application Disclosure Gazettes Nos. 1989-180444 and 1991-17542 describe high precision measuring methods for thermal conductivity of fluid utilizing the unsteady state hot-wire method. The method utilizing the unsteady state hot-wire method as disclosed in the former Disclosure Gazette No. 1989-180444 takes account of a measurement error due to, an electric resistance appearing in a bridge used to read-out a signal output from the sensor.

The method described in the latter Disclosure Gazette No. 1991-17542 determines the thermal conductivity based on a linear relationship established between a temperature rise and a period of energization in order to eliminate an influence of convective heat transfer occurring in the fluid on the measurement utilizing the unsteady state hot-wire method.

These two prior techniques are basically different from the steady slate hot-wire method according to the present invention in that they adopt the unsteady state filament heating method. The unsteady state hot-wire method had an intrinsic drawback such that a value obtained from direct measurement must be processed to determine a thermal conductivity. Particularly, the hot-wire method described in the Disclosure Gazette No. 1989-180444 involves various factors that must be taken into account for determination of the thermal conductivity such as changes in resistance as well as in temperature and a range of temperature.

It is also difficult for these two prior techniques to be effectively incorporated in production lines because of their intrinsic drawbacks such that the measurement is batch-based, the metallic thin wire employed has a poor resistance against vibration and the apparatus itself is readily affected by a change in the environmental temperature.

SUMMARY OF THE INVENTION

Accordingly, it is a primary object of the invention to provide method and apparatus utilizing the steady state hot-wire technique to measure a thermal conductivity of fluid at a low cost, based on an index value well correlated with the thermal conductivity in a manner free from undesirable effect of a convective heat transfer possibly occurring in the fluid to be measured and, if desired, said apparatus being adapted for in-line measurement on an actual site of production.

The object set forth above is achieved, according to the invention, by a method comprising the steps of disposing a heating sensor adapted not only to generate heat but also to measure its own temperature in a pipe wherein a clearance defined between the inner wall of the pipe and the outer wall of the heating sensor is dimensioned so that the measurement can be free from any influence of a heat conductive heat transfer due to a convection caused by generation of heat from the heat sensor, measuring a temperature of the fluid, measuring a temperature of the heating sensor itself, determining a differential temperature therebetween in steady state, and determining the thermal conductivity of this fluid based on a correlation between the differential temperature and the thermal conductivity.

A. A CLEARANCE BETWEEN THE HEATING SENSOR AND THE HOLLOW CYLINDER OR THE PIPE IN WHICH THE HEATING SENSOR IS DISPOSED

Namely, the clearance defined between the outer diameter of the sensor and the inner wall of the pipe containing this sensor significantly affects the measurement and an excessively large clearance would generate a convection in the fluid to be measured during the measurement in steady state. Consequently, a convective heat transfer would occur in addition to a conductive heat transfer and such convective heat transfer would seriously affect the measurement of the thermal conductivity, making the accurate measurement impossible.

Theoretically it is preferred to dimension the clearance as narrow as possible, but excessively narrow clearance would result in practical inconveniences, for example, such excessively narrow clearance would make it difficult to fabricate the sensor with high precision and maintenance of the instrument as well as exchange of the fluid to be measured in preparation for each measurement would require a lot of time. From such viewpoint, it is rather preferred to dimension the clearance as wide as possible so far as it is smaller than an allowable limit.

It should be understood that a convection possibly generated in the fluid due to heat conduction thereof can not be completely eliminated during the measurement in steady state even if the clearance is dimensioned considerably narrow. However, a rising flow and a descending flow occur without disorder in the fluid in this clearance, and a temperature distribution is found regularly along the center line of the heating element in the direction of the length of the heating sensor, which result in the same state as if there is no convection found in the fluid. The present invention overcomes this problem by utilizing an adequately high correlation between an index value and the thermal conductivity obtained in a state, in which the influence of the heat transfer by convection is practically negligible compared to that of the heat transfer by conduction.

B. THE METHOD FOR DETERMINING THE CLEARANCE IN THE INVENTION

Generally, two different procedures may be selectively employed to determine the specific width of the clearance. The first procedure is to observe a temperature distribution in the fluid until it is experimentally detected that a uniform temperature distribution, with no convection, is attained and in which an equal temperature line is parallel to the center line of the heating element. While such procedure allows a high reliability to be obtained, a lot of time is taken before completion of the procedure because a uniform temperature distribution should be detected for every sensor and for every sample of fluid. Unless equal temperature lines of temperature distribution is parallel to the center line of the heating element, any experimental data can not be used to determine the clearance since any non-uniformity remaining in the temperature distribution is considered to reflect a presence of convection.

The second procedure is to find the optimal clearance by varying the clearance. Specifically, while the clearance is varied, an index value is obtained using a reference material, and then a coefficient of correlation between this index value and the thermal conductivity of this reference material is derived by the well known method. Thus a diameter, a clearance and a coefficient of correlation established therebetween may be determined for the particular sensor with a sufficiently high and practically useful range of the coefficient of correlation between the reference material's thermal conductivity and the index value with this, the optimal clearance associated with this particular sensor may be determined.

The clearance can be practically determined on the basis of the coefficients of correlation so far as these coefficients are at least 0.995, utilizing this method of determining the clearance from determined coefficients of correlation between the index value and the thermal conductivity of the reference material.

When the cylindrical heating sensor is used, a lower limit dimension of the clearance can be calculated on the basis of factors such as a diameter of the heating sensor.

The inventor has experimentally found that a clearance of less than 0.8 mm in association with the heating sensor of a diameter less than 3.5 mm will allow samples of fluid to be maintained in substantially steady state in which the influence of heat transfer by convection in the samples of fluid will be practically negligible.

C. THE SPACER MEANS

As one of the technical means adapted to maintain a predetermined clearance, a clearance can be obtained by a movable or a stationary spacer means being held at an appropriate distance from the heating sensor's outer surface.

The spacer means may be of any configuration so far as a desired clearance can be maintained between the line's inner wall and the heat generating surface of the heating sensor.

Accordingly, the spacer means may be of various types such as a type adapted to be put on the sensor surface, a type adapted to be segmented and a type adapted to be adjustably movable so far as the clearance can function properly.

Concerning the relation between the clearance and the heating sensor, the heating sensor can be of any configuration. For example, if the heating sensor is cylindrical, the spacer means may be cylindrically configured to surround said sensor with a desired clearance from the surface of said sensor. If the heating sensor is in the form of planar plate, the spacer means also may be a planar plate adapted to be adjustably mounted so as to maintain a desired clearance from the heating surface of said planar plate.

D. THE TEMPERATURE OF THE HEATING SENSOR

The expression "temperature of the heating sensor" used previously for description of the inventive method may be an average temperature of a heating element contained within the heating sensor or a surface temperature of the heating sensor calculated on the basis of a relationship established between the temperature of the heating element, and the thermal conductivity and the thickness of the sensor protecting tube. The procedure to determine surface temperature of the sensor is proposed by some of the inventors of the present invention in Japanese patent application disclosure Gazette No. 1988-217261.

E. THE TEMPERATURE OF THE FLUID BEING MEASURED

While, in the present invention, the fluid temperature may be measured by any separate thermometric element or substituted by the temperature of the thermostatic fluid, it is more convenient to control the electric current supplied to the heating sensor so as to functionally convert the sensor to a thermometric element by which the fluid temperature can be measured. In this manner, such functional conversion through control off the electric current supplied to the sensor allows the heating sensor to function selectively as the thermometric element used to measure the temperature of the fluid to be measured or as the heating sensor adapted for measurement of its own temperature.

In case that the fluid temperature is substituted by a temperature of the thermostatic fluid, the heat transfer characteristic of a particular material from which the said cylindrical pipe is made must be taken into account (such as utilizing material of high thermal conductivity).

F. THE METHOD FOR CALCULATING THE THERMAL CONDUCTIVITY OF THE FLUID BEING MEASURED

While the present invention basically utilizes the differential temperature between the temperature of the heating sensor and the temperature of the fluid to be measured as the index value for the thermal conductivity of this fluid, it is also possible to utilize the differential temperature between the temperature of the heating sensor and the temperature of the thermostatic fluid as the index value and thereby to facilitate the operation of measurement.

In addition to the method determining the thermal conductivity of the fluid based on the correlation established between the thermal conductivity of the fluid and said differential temperature, the thermal conductivity of the fluid can be determined on the basis of a correlation established between a heating value provided by the heating sensor and the thermal conductivity of the fluid, by controlling heat generation so as to maintain a constant differential temperature between the fluid and the heating sensor in a steady state.

The fluid confined within a cylindrical pipe is required to be maintained at a constant temperature by using thermostatic means. Specifically, it is preferably to enclose the pipe containing the said heating sensor by the thermostatic means partially or wholly, or to enclose the apparatus itself by the thermostatic means entirely.

It is also possible to arrange the thermostatic means so that a temperature of the thermostatic fluid supplied to a thermostatic tank is controlled so as to follow a temperature of the sampled fluid. The thermostatic means may comprise a multiple cylindrical pipe so that the sensor is placed within the inner pipe and the thermostatic fluid flow through the outer pipe of the multiple pipe.

The present invention provides an effect as will be described below.

Method and apparatus of the invention allow a thermal conductivity of fluid to be easily measured in a production line and thereby facilitate a manufacturing process to be controlled.

Moreover, accurate measurement can be achieved without being affected by changes in the environmental temperature on an actual site at which the apparatus is installed, since the fluid being measured is maintained at a predetermined temperature under the effect of the thermostatic fluid according to the one embodiment of the invention as has been described above.

A unique method of the invention wherein the thermal conductivity is determined on the basis of a relationship established between a differential temperature of the fluid being measured and the sensor, on one hand, and said thermal conductivity, on the other hand, allows the measurement to be achieved without requiring either complex numeric processing or computing circuit and thereby allows the apparatus itself to be realized at reasonably low cost.

Additionally, tile invention allows the apparatus to be structurally simplified with respect to the well known apparatus used for the conventional steady state hot-wire method and correspondingly facilitates various operations such as washing and maintenance. Accordingly, the apparatus can be installed directly in the actual production line.

BRIEF DESCRIPTION OF THE DRAWINGS

The above and other objects of the invention will be seen by reference to the description taken in connection with the accompanying drawings, in which.

DETAILED DESCRIPTION OF THE INVENTION

The invention will be described by way of example in reference with the accompanying drawings.

Figure 1:
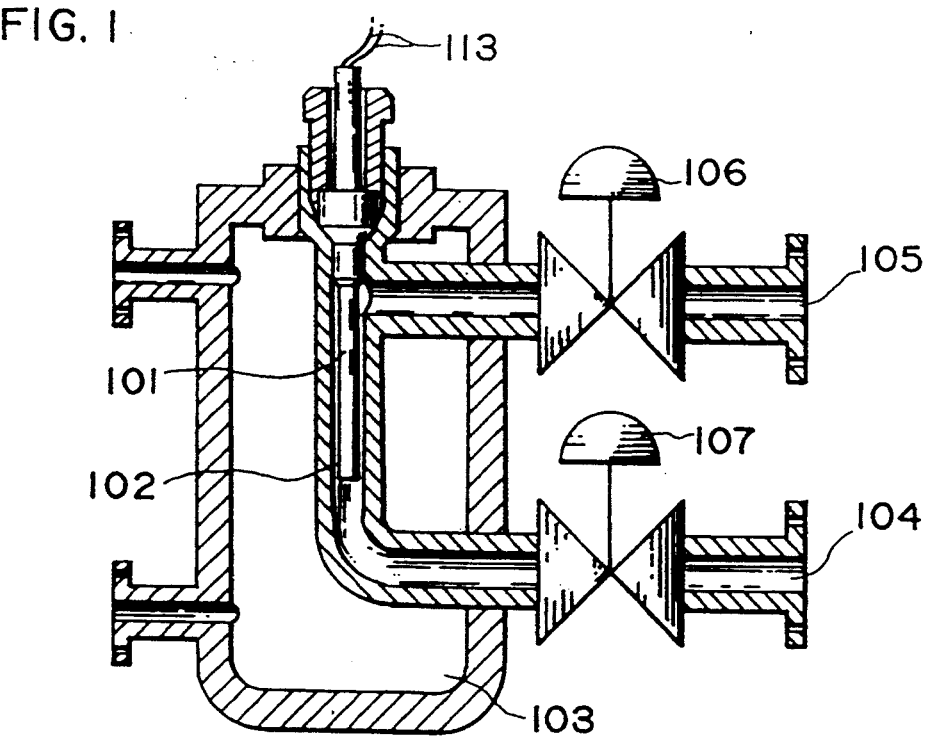
FIG. 1 is a sectional view, taken in an axial direction, showing first embodiment of an apparatus used for a measuring method of the invention.

Referring to FIG. 1, there is shown a first embodiment of the heating sensor to perform the inventive method, in which a cylindrical pipe 102 containing a heating sensor 101 extends through a thermostatic bed 103. Reference numerals 104 and 105 designate inlet and outlet, respectively, through which the fluid to be measured flows into and out from the cylindrical pipe 102, respectively. Specifically, the fluid to be measured is pumped into the cylindrical pipe 102 and, after a predetermined quantity of the fluid has passed through the pipe 102, a valve 106 provided immediately upstream of the outlet 105 is closed, whereupon another valve 107 provided immediately downstream of the inlet 104 is closed so as to stop further flow within the cylindrical pipe 102. Alternatively, a stepping motor or the like may be used, instead of using those valves 106, 107, to introduce the fluid into the cylindrical pipe 102 so that the flow within the cylindrical pipe 102 may be intermittently slopped.

Preferably, the heating sensor 101 is vertically arranged as shown. Such arrangement allows air bubbles or the like often generated in the fluid to be prevented from staying on the surface of the sensor 101 and thereby assures homogeneity of the fluid. In this manner, any significant measurement error can be avoided.

Particularly when the heating sensor 101 is of a relatively small diameter, a clearance defined between outer diameter of the heating sensor 101 and inner wall of the cylindrical pipe 102 will be correspondingly reduced and a correspondingly higher pressure will be required to drive the fluid. Consequently, the heating sensor 101 will be apt to be deformed under such higher pressure. However, such disadvantageous deformation of the heating sensor 101 itself can be effectively avoided by arranging the heating sensor in vertical posture as shown, since the pressure at which the fluid is driven is directed axially of the heating sensor 101.

Figure 2:
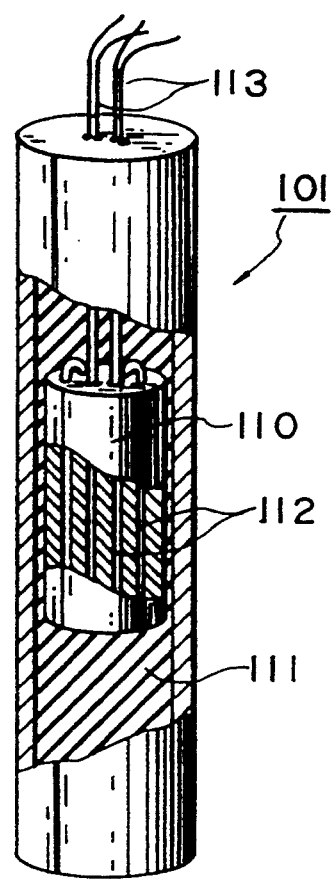
FIG. 2 is a perspective view showing, as partially broken away, a cylindrical heating sensor used for the measuring method of the invention.

Referring to FIG. 2, the heating sensor 101 comprises a heating element 110 encased within an insulator 111 and a heating wire (metallic thin wire) 112 embedded in the heating element 110 so as to be supplied via lead wires 113 with electric current. The arrangement as has been described is basically similar to the heating sensor arrangement disclosed in Japanese patent application Disclosure Gazette No. 1989-44838.

Figure 3:
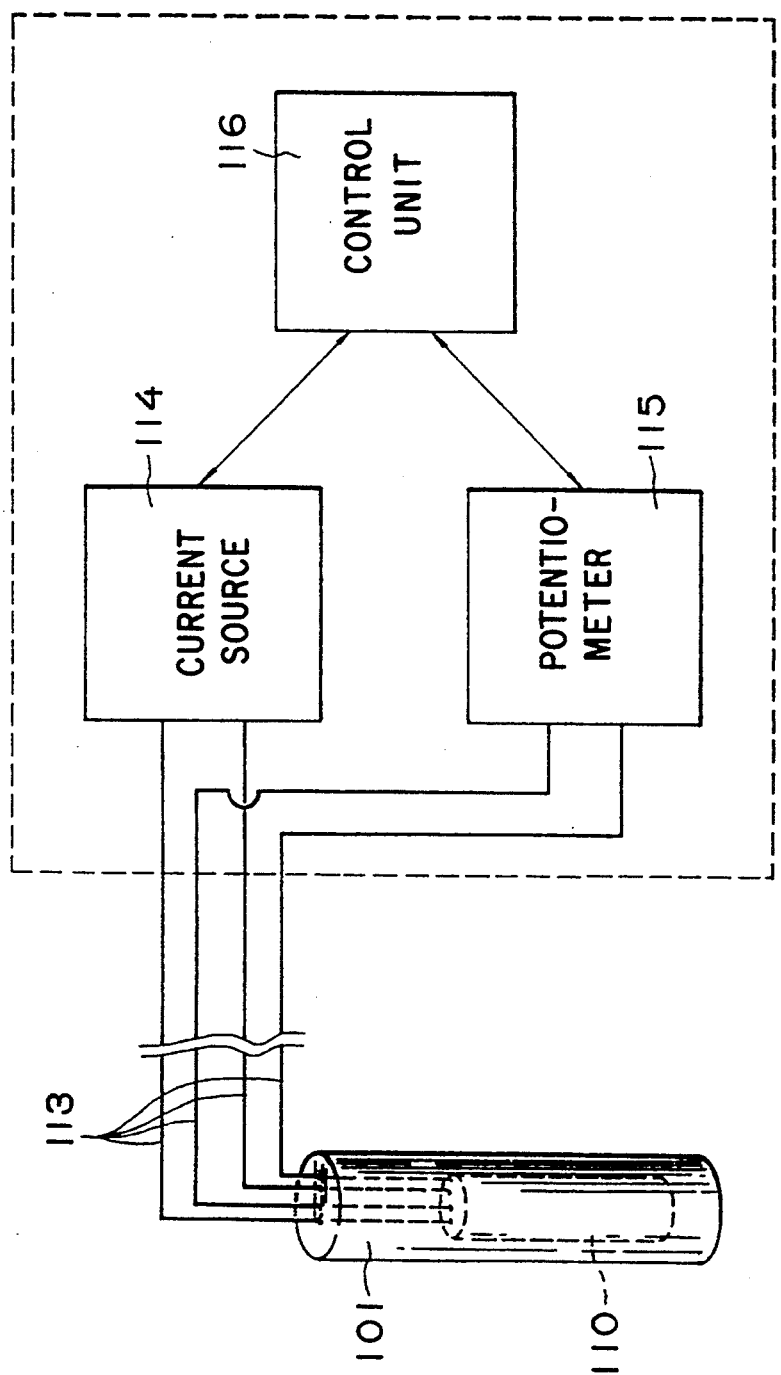
FIG. 3 is a schematic wiring diagram of a control unit used to control a heating element of the invention.

Referring to FIG. 3, the lead wires 113 connected to the heating element 110 are connected to a current source 114, on one hand, and to a potentiometer 115, on the other hand, the latter two components 114, 115 being connected to a control unit 116.

The heating sensor 101 constructed as mentioned above is disposed within the cylindrical pipe 102 and supplied via the lead wires 113 with electric current, causing the heating element 110 to generate heat so that a temperature of the heating sensor 101 itself may be measured based on a change appearing in a resistance value of the heating wire 112 contained therein. Then, the quantity of fluid now held within the cylindrical pipe 102 in order to be measured is maintained at a predetermined temperature against the heating effect of the sensor under the effect of a thermostatic fluid (e.g., water) circulating through the thermostatic bed 103 and, in a steady state thus maintained, a thermal conductivity of the fluid to be measured is obtained based on a differential temperature between the heating sensor 101 and the fluid to be measured.

It should be understood that the heating sensor 101 may be used as means adapted to measure its own temperature during heat generation from the heating element 110 which is applied via the lead wires 113 with appropriate voltage and, in addition, as a merely thermometric sensor adapted to measure a temperature of the fluid based on value of voltage appearing across the heating element 110 as the latter is supplied with substantially negligible weak current causing heat generation therefrom which is of a sufficiently low value. In this manner it is possible for one and same heating sensor 101 to measure temperatures of both the fluid and the sensor itself and thereby to determine a differential temperature therebetween.

Obviously, there may be separately provided a thermometric sensor to measure a temperature of the fluid.

The clearance defined between outer wall of the heating sensor 101 and inner wall of the cylindrical pipe 102 must be dimensioned so that the measurement can be free from any significant influence of a convective heat transfer even if a convection is generated in the fluid being measured due to a temperature rise caused by heating of the sensor.

The clearance principally depends on an outer diameter of the heating sensor 101 and an inner diameter of the cylindrical pipe 102. However, the clearance largely depends also on a viscosity of the fluid, i.e., the clearance may be dimensioned relatively large for the fluid having a relatively high viscosity, since the convection is not easily generated in the fluid of such high viscosity. The clearance depends also on the other various factors such as heating value of the sensor 101, configuration of the sensor 101, and length of the heating element 112 contained therein.

As previously mentioned, the clearance can be experimentally determined or can be determined using the coefficient of correlation. Now determination of the clearance will be considered with respect to the latter case.

Figure 4:
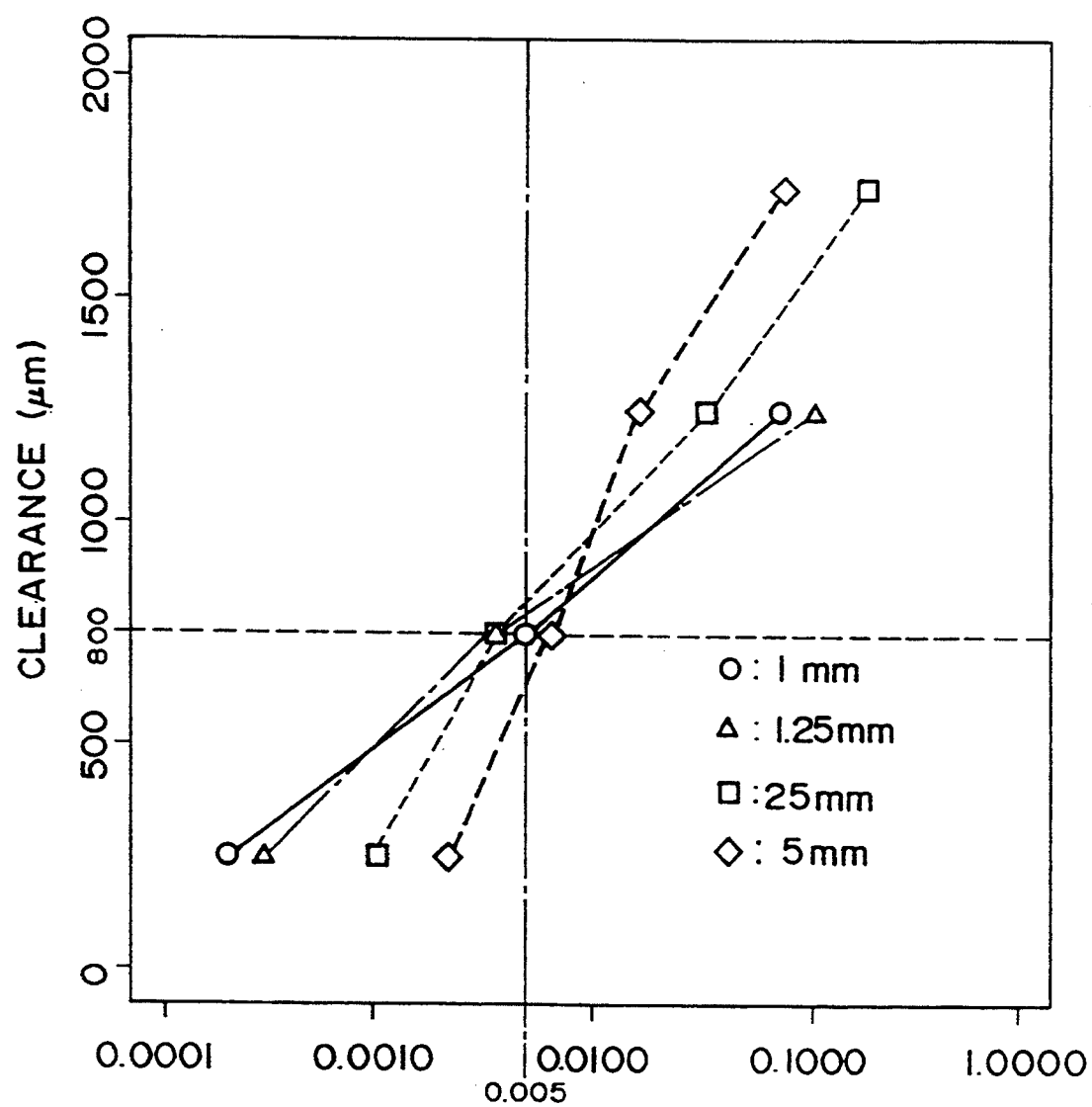
FIG. 4 is a graphic diagram plotting clearance versus correlation coefficient for the cases of respective heating sensors having radius of 1 mm, 1.25 mm, 2.5 mm and 5 mm.

FIG. 4 indicates coefficients of correlation having been detected for the sensors having radius of 1 mm, 1.24 mm, 2.5 mm and 5 mm and it will be apparent that the coefficient of correlation is 0.995 or higher for the clearance less than 0.8 mm and such clearance can be determined to be useful.

While even a clearance in the order of 2 mm might be used if a precision is not important, it is desirable to dimension the clearance less than 0.8 mm so as to obtain a coefficient of correlation of at least 0.995 assuring that the measurement should be achieved without being significantly affected by a convective heat transfer possibly generated in the fluid being measured.

Figure 5:
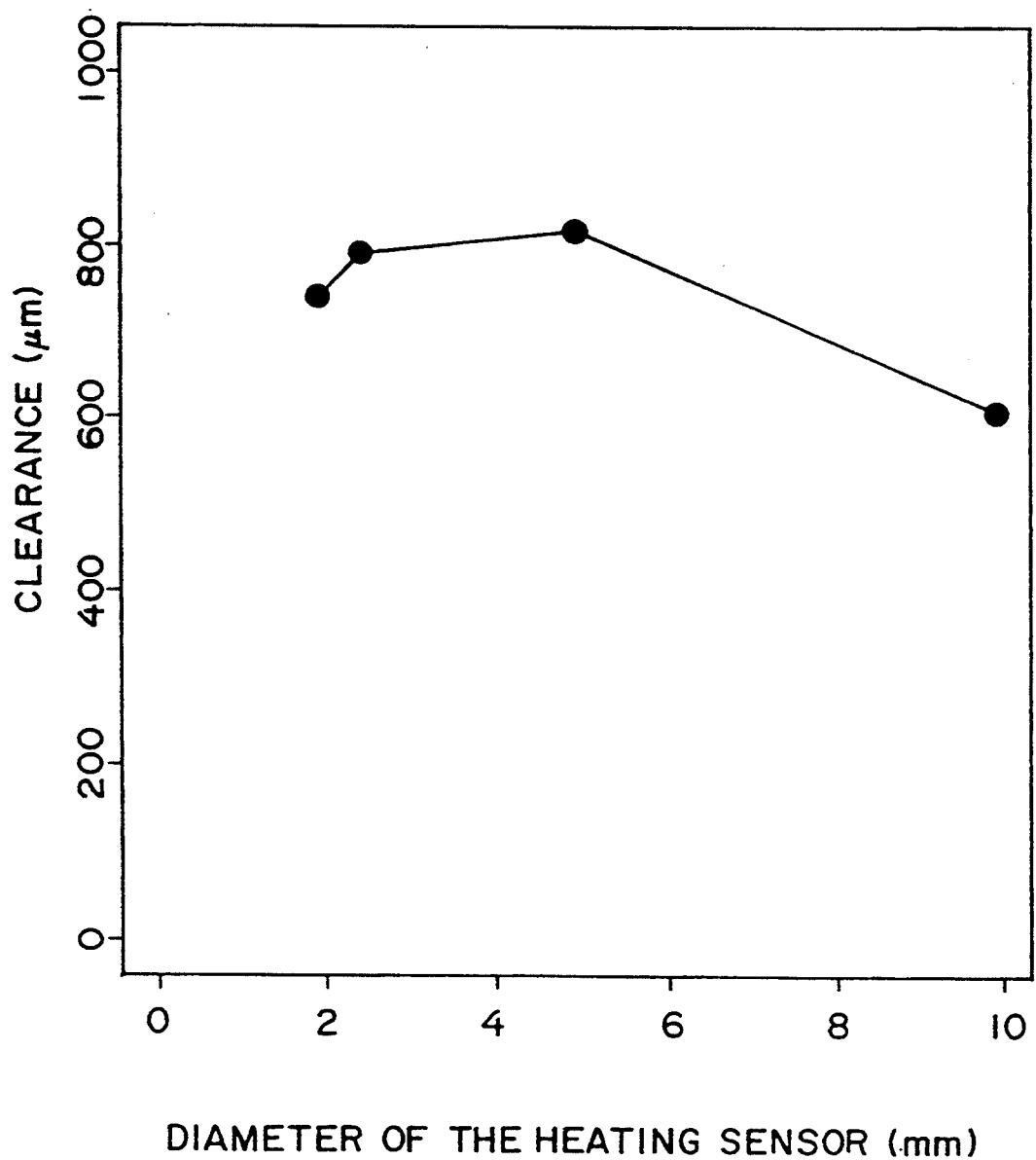
FIG. 5 is a graphic diagram plotting clearance versus diameter of the heating sensor when the fluid is under the conditions that a coefficient of correlation is 0.995 and a heating value is constant.

FIG. 5 plots diameter of the heating sensor 101 versus clearance for the case in which the fluid whose coefficient of correlation is 0.995 is used, and the heating value is constant, showing the maximum clearance which can be dimensioned for a given diameter of the heating sensor.

The graphic diagram of FIG. 5 indicates that the maximum value of the clearance which is able to assure the coefficient of correlation of 0.995 is limited to 0.8 mm.

It should be understood that the determination of the clearance was based on the experimental value obtained with use of the heating sensor having a diameter less than 3.5 mm and on the numerical analysis with the use of the heating sensor having a diameter more than 3.5 mm. As will be apparent, the clearance value determined by the numeric analysis is well in coincidence with the experimental result so far as the sensor's diameter is less than 3.5 mm, verifying that the detection of clearance based on the coefficient of correlation is valid.

It is well known that, when the measurement is performed in steady state by the apparatus of a type as shown by FIG. 1, there is established between differential temperature $\Delta\theta_W$ and thermal conductivity $\lambda$ of the fluid being measured a relationship as follows:

$$\Delta\theta_w = \frac{Q\ln(r_2/r_1)}{2\pi L} \times \frac{1}{\lambda} + C \tag{1}$$

where
Q: heating value(W)
L: length of the heating element(m)
$r_2$: inner diameter of outer cylinder(m)
$r_1$: outer diameter of cylindrical heating sensor(m)
$\Delta\theta_W$: difference between average temperature of sensor and temperature of fluid.
C: constant (°C.)

This equation (1) may be used to determine the thermal conductivity $\lambda$ on the basis of differential temperature $\Delta\theta_W$ and the differential temperature $\Delta\theta_W$ may be controlled at a constant value to determine the thermal conductivity based on the correlation between a change in the heating value Q and the thermal conductivity $\lambda$.

Determination of the thermal conductivity $\lambda$ based on the correlation between differential temperature $\Delta\theta_W$ and thermal conductivity $\lambda$ will be exemplarily described below.

Figure 6:
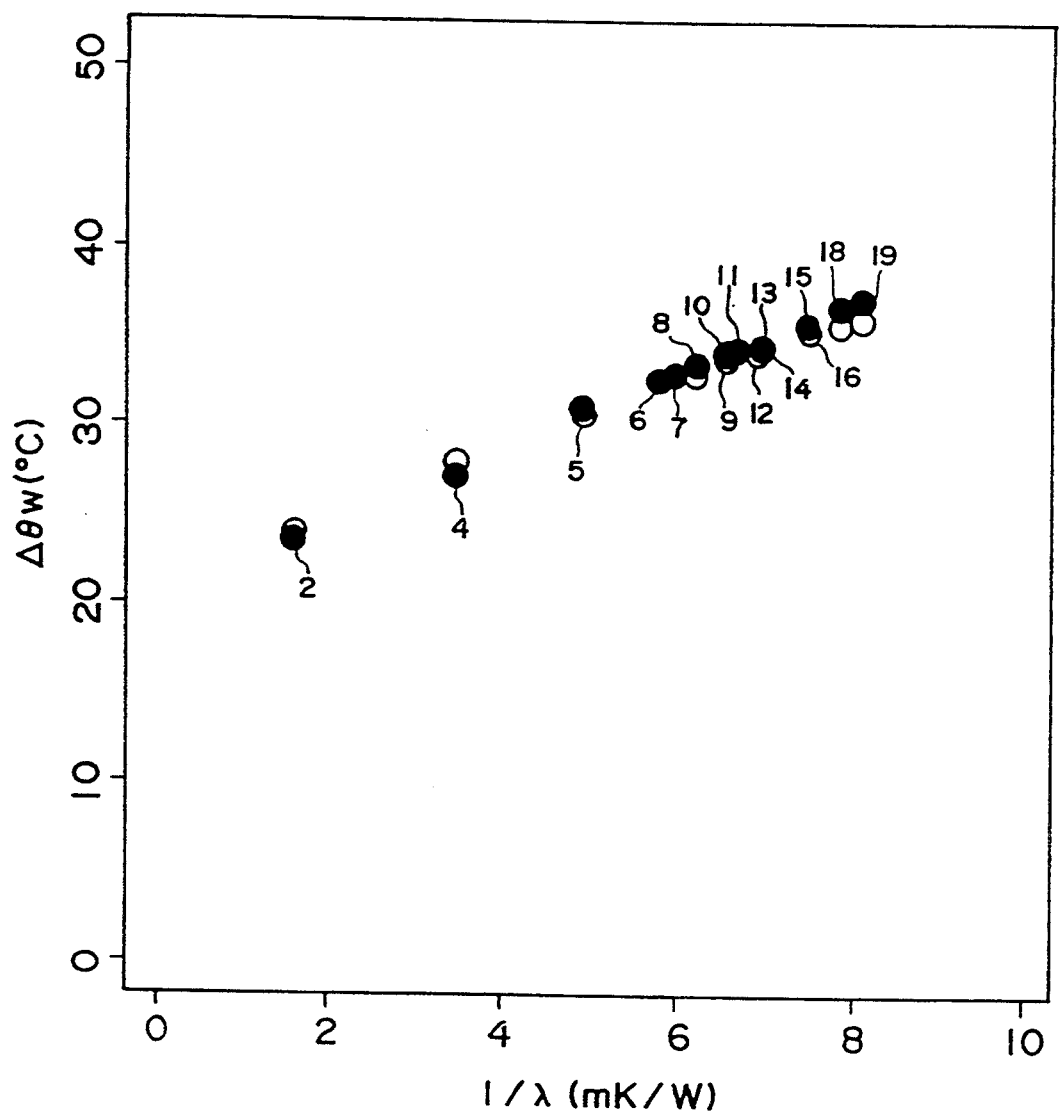
FIGS. 6 and 7 are graphic diagrams respectively plotting temperature difference $\Delta\theta_W$ between average temperature of the heating sensor and a temperature of the fluid being measured versus value of reciprocal of $\lambda$ ($\lambda$: thermal conductivity of the fluid being measured), these values having been determined in steady state mode using the inventive method with a thermostat bed being maintained at a temperature of 25° C.
Figure 7:
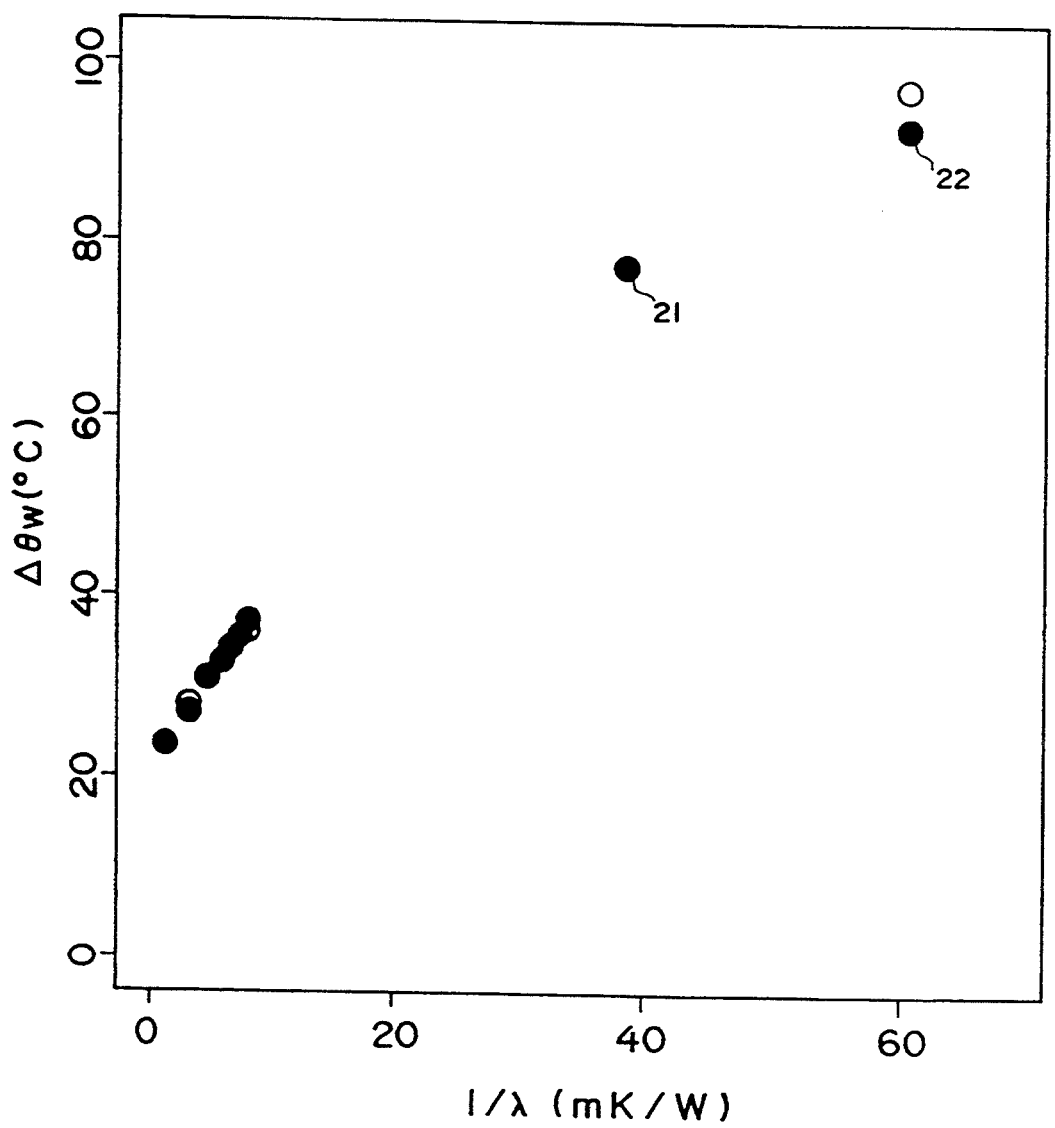

FIGS. 6 and 7 respectively plot differential temperature $\Delta\theta_W$ between the sensor 101 and the fluid being measured versus the reciprocal of thermal conductivity $\lambda$ of the fluid being measured when the measurement was performed in steady state with the apparatus of a type as shown by FIG. 1 while the fluid being measured is maintained at a temperature of 25° C. under the effect of the thermostatic bed 103.

It should be understood that FIGS. 6 and 7 adopt different manners in which the reciprocal of thermal conductivity $\lambda$ is scaled on the axis of the abscissa and relate to different objects to be measured, respectively, i.e., FIG. 6 relates to liquids while FIG. 7 relates to gases. Dots in these figures indicate relationships between the differential temperatures $\Delta\theta_W$ and the associated reciprocal of thermal conductivities exhibited by respective substances, as will be listed in Table 1. Black dots indicate experimentally obtained values and white dots indicate values obtained by numeric analysis. Numbers in these figures correspond to substance numbers in Table 1.

TABLE 1

| No. | Substances | Thermal conductivity (W/mk) |
|---|---|---|
| 1. | mercury | 8.130 |
| 2. | water | 0.610 |
| 3. | heavy water | 0.592 |
| 4. | glycerine | 0.287 |
| 5. | methanol | 0.203 |
| 6. | aniline | 0.172 |
| 7. | ethanol | 0.167 |
| 8. | acetone | 0.160 |
| 9. | n-propanol | 0.152 |
| 10. | n-butanol | 0.152 |
| 11. | *helium | 0.149 |
| 12. | methyl ethyl ketone | 0.144 |
| 13. | methyl acetate | 0.143 |
| 14. | benzene | 0.143 |
| 15. | pentanol | 0.134 |
| 16. | toluene | 0.133 |
| 17. | n-octane | 0.130 |
| 18. | n-heptane | 0.127 |
| 19. | n-hexane | 0.123 |
| 20. | R113 | 0.0733 |
| 21. | *air | 0.0259 |
| 22. | *carbon dioxide | 0.0165 |

*gases

As will be appreciated from FIGS. 6 and 7, the result of the numeric analysis well coincides with the experimental result, and it is verified that the result of measurement can be estimated from the numeric analysis.

In order that the thermal conductivity λ of fluid can be measured in steady and convection-free state as has been described above, it is important to adjust the clearance to the optical size as previously mentioned. With the clearance dimensioned so that no convection should be generated or, even if a convection is generated, the measurement of thermal conductivity should not be affected by a heat transfer due to such convection, a series of experiments were made and result listed in Table 2 was obtained.

cordingly, when different kinds of fluid are intermittently introduced into the cylindrical pipe one kind of fluid at a time, each kind of fluid can be reliably identified.

Also for a particular kind of fluid having its thermal conductivity changing as the time elapses, so long as a correlation between such change in the thermal conductivity and said differential temperature $\Delta\theta_S$ has previously been determined it is possible to determine a thermal conductivity of said fluid. Based on such change in the thermal conductivity, it is also possible to detect a change in concentration of the fluid or change in structure or composition thereof. Furthermore, such change in thermal conductivity may be computationally processed so as to be used by such as the production line control system.

In an example of the production line control, a change in concentration may be detected as a change in thermal conductivity and a flow in the said production line may be controlled depending on a degree of such change. As has been mentioned, thermostatic fluid may be maintained at a constant temperature or controlled to follow a temperature of the fluid being measured to determine the thermal conductivity in the manner as previously mentioned.

Figure 8:
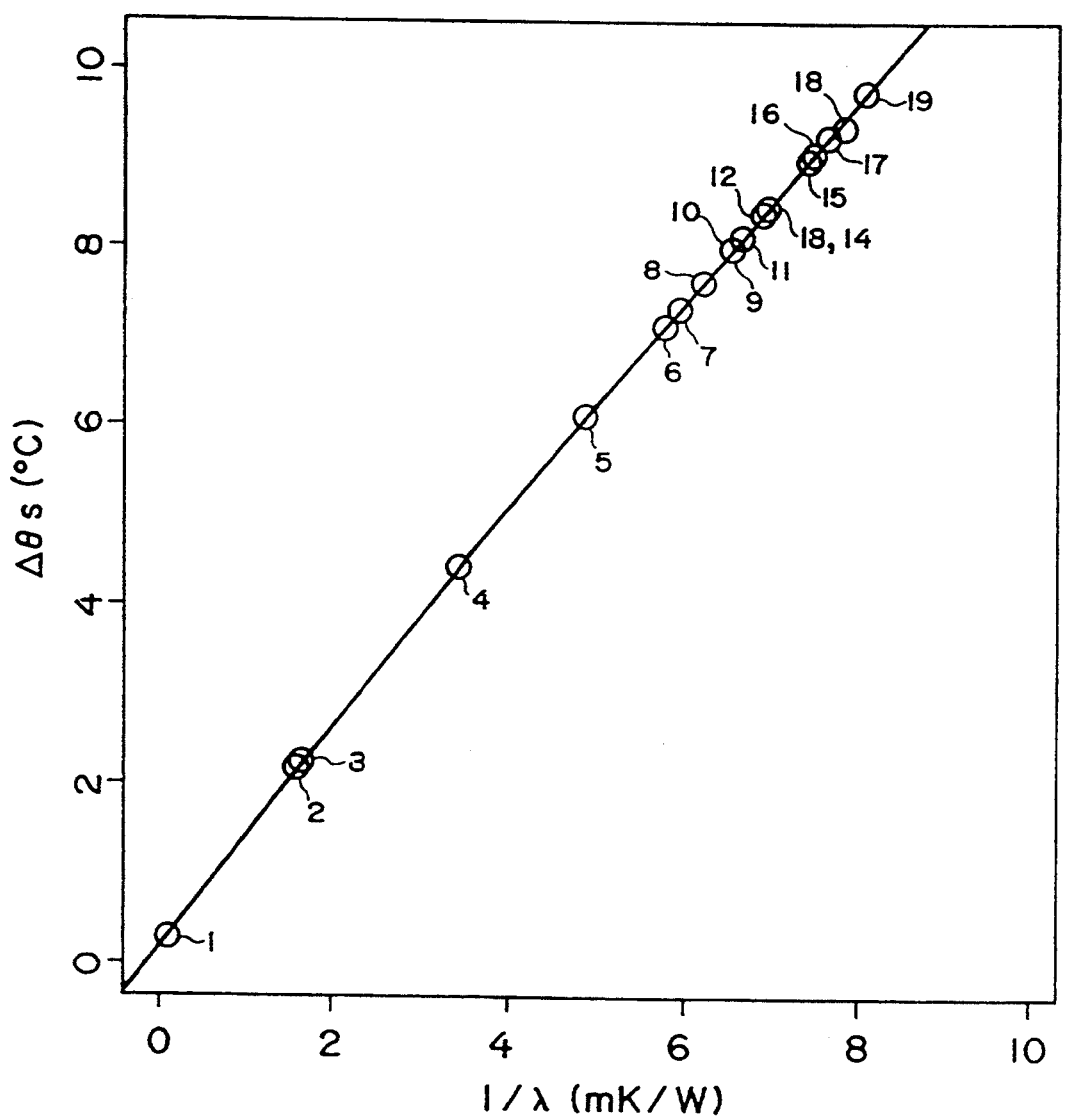
FIGS. 8 and 9 are graphic diagrams respectively plotting temperature difference $\Delta\theta_S$ between the heating sensor's surface and the fluid being measured versus value of reciprocal of thermal conductivity derived by numeric analysis.
Figure 9:
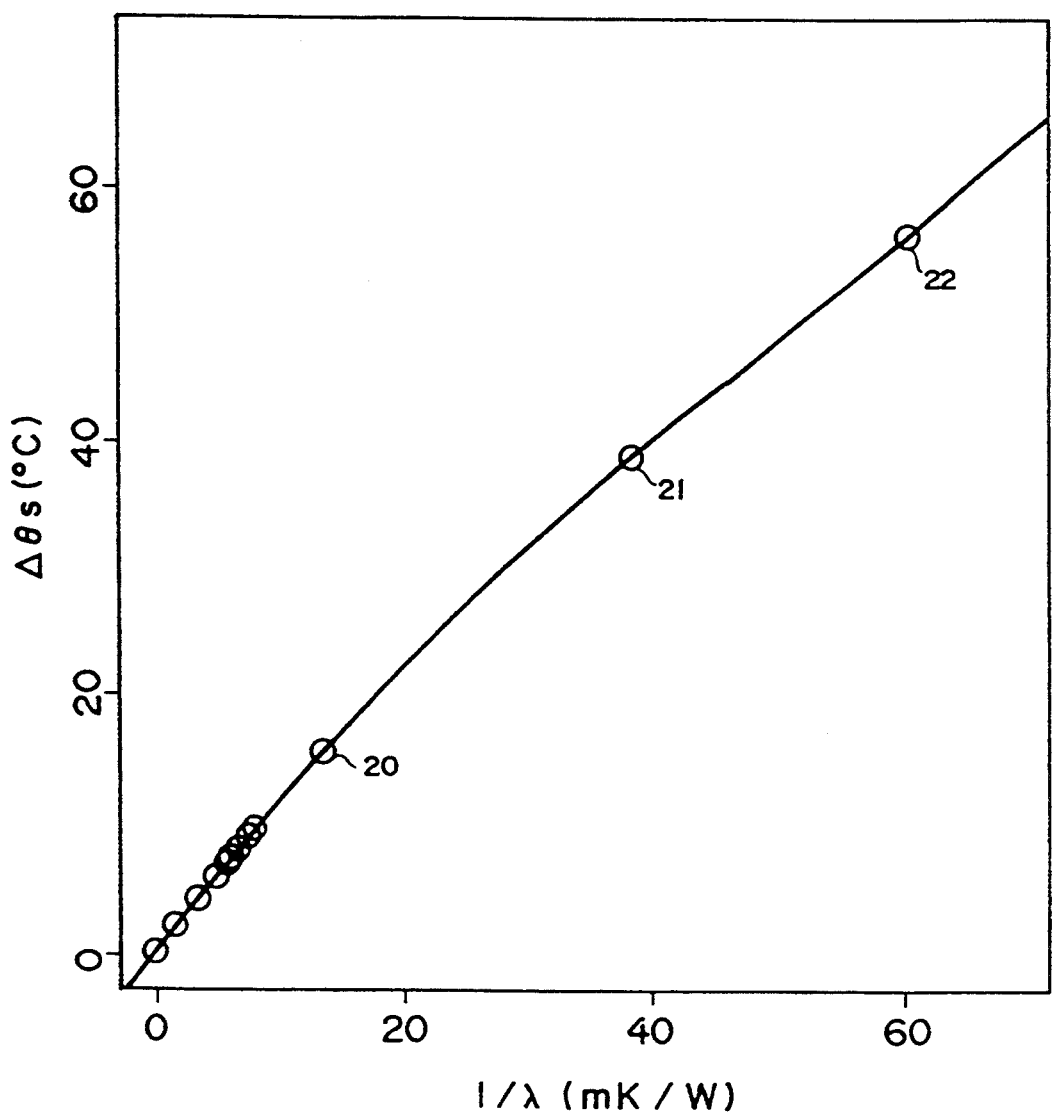

FIGS. 8 and 9 respectively plot differential temperature $\Delta\theta_S$ versus the reciprocal of thermal conductivity obtained by numeric analysis and it will be apparent also from these figures that the thermal conductivity obtained by numeric analysis substantially coincides with the actually measured thermal conductivity.

In these embodiments, a series of experiments were made under the condition: the sensor having a diameter of 2.5 mm; the clearance of 0.75 mm; and the heating value of 1 W.

The thermal conductivity λ may be obtained from the actually measured values as listed in Table 2, according to a regression formula:

TABLE 2

| FLUID SAMPLE | THERMAL CONDUCTIVITY (W/mK) (LITERATURE-VALUE 25° C.) | $\Delta\theta_W$ EXPERIMENTAL VALUES (°C.) | $\Delta\theta_S$ BASED ON NUMERIC ANALYSIS (°C.) | THERMAL CONDUCTIVITY (W/mK) OBTAINED BY REGRESSION |
|---|---|---|---|---|
| water | 0.610 | 23.61 | 4.188 | 0.599 |
| glycerine | 0.287 | 27.25 | 8.350 | 0.300 |
| methanol | 0.203 | 31.12 | 11.155 | 0.195 |
| aniline | 0.172 | 32.72 | 13.078 | 0.170 |
| ethanol | 0.167 | 33.17 | 13.313 | 0.164 |
| acetone | 0.160 | 33.63 | 13.227 | 0.158 |
| n-propanol | 0.152 | 34.04 | 14.502 | 0.153 |
| n-butanol | 0.152 | 34.33 | 14.527 | 0.150 |
| **helium | 0.149 | 34.40 | 14.815 | 0.149 |
| methyl ethyl ketone | 0.144 | 34.53 | 14.568 | 0.148 |
| benzene | 0.143 | 34.92 | 14.981 | 0.144 |
| pentanol | 0.134 | 35.90 | 15.900 | 0.134 |
| toluene | 0.133 | 35.99 | 15.929 | 0.134 |
| n-heptane | 0.130 | 37.07 | 16.238 | 0.130 |
| n-hexane | 0.123 | 37.38 | 16.506 | 0.123 |
| **air | 0.0259 | 77.76 | 58.211 | 0.0259 |
| **carbon-dioxide | 0.165 | 93.71 | 78.362 | 0.0165 |

**gases

FIGS. 8 and 9 graphically show the results of numerical analysis based on the differential temperature $\Delta\theta_S$ between the sensor surface and the fluid being measured, utilizing the samples of fluid shown in Table 1. These relationships may be previously determined and the differential temperature $\Delta\theta_S$ may be obtained to determine a thermal conductivity of the particular fluid within the cylindrical pipe, based on which, in turn, it is possible to identify what the fluid in question is. Ac- $$\lambda = 1/(A + B \times \Delta\theta_W + C \times \Delta\theta_W^2 + D \times \Delta\theta_W^3)$$

Coefficients A,B,C and D take specific values as follow:

A = −1.0398 E1
B = 6.1081 E−1

C = −6.1724 E−3
D = 8.2584 E−5

Figure 10:
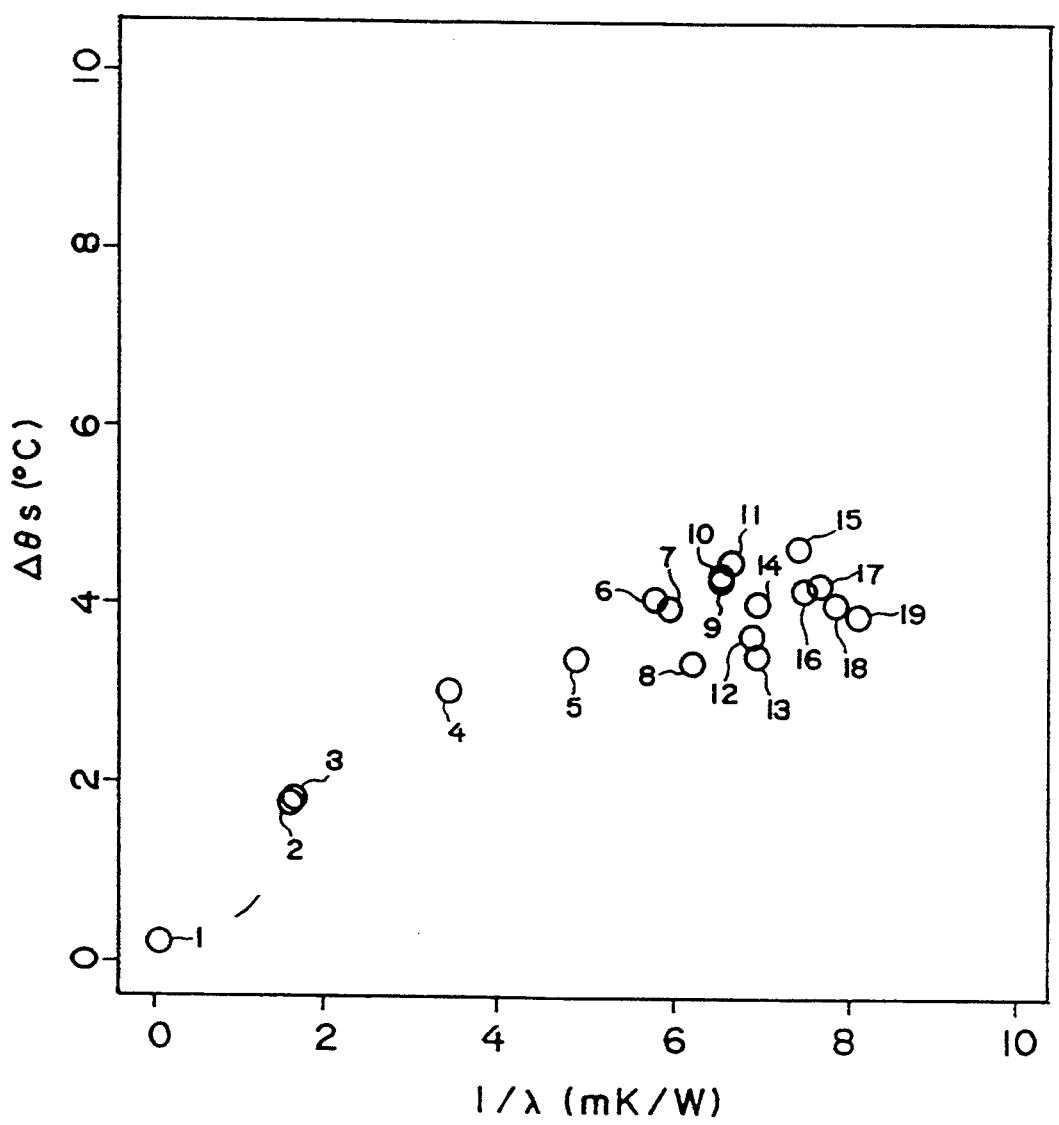
FIGS. 10 and 11 are graphic diagrams respectively plotting temperature difference $\Delta\theta_S$ corresponding to an influence of convective heat transfer upon measurement of thermal conductivity versus reciprocal of $\lambda$ ($\lambda$: thermal conductivity)
Figure 11:
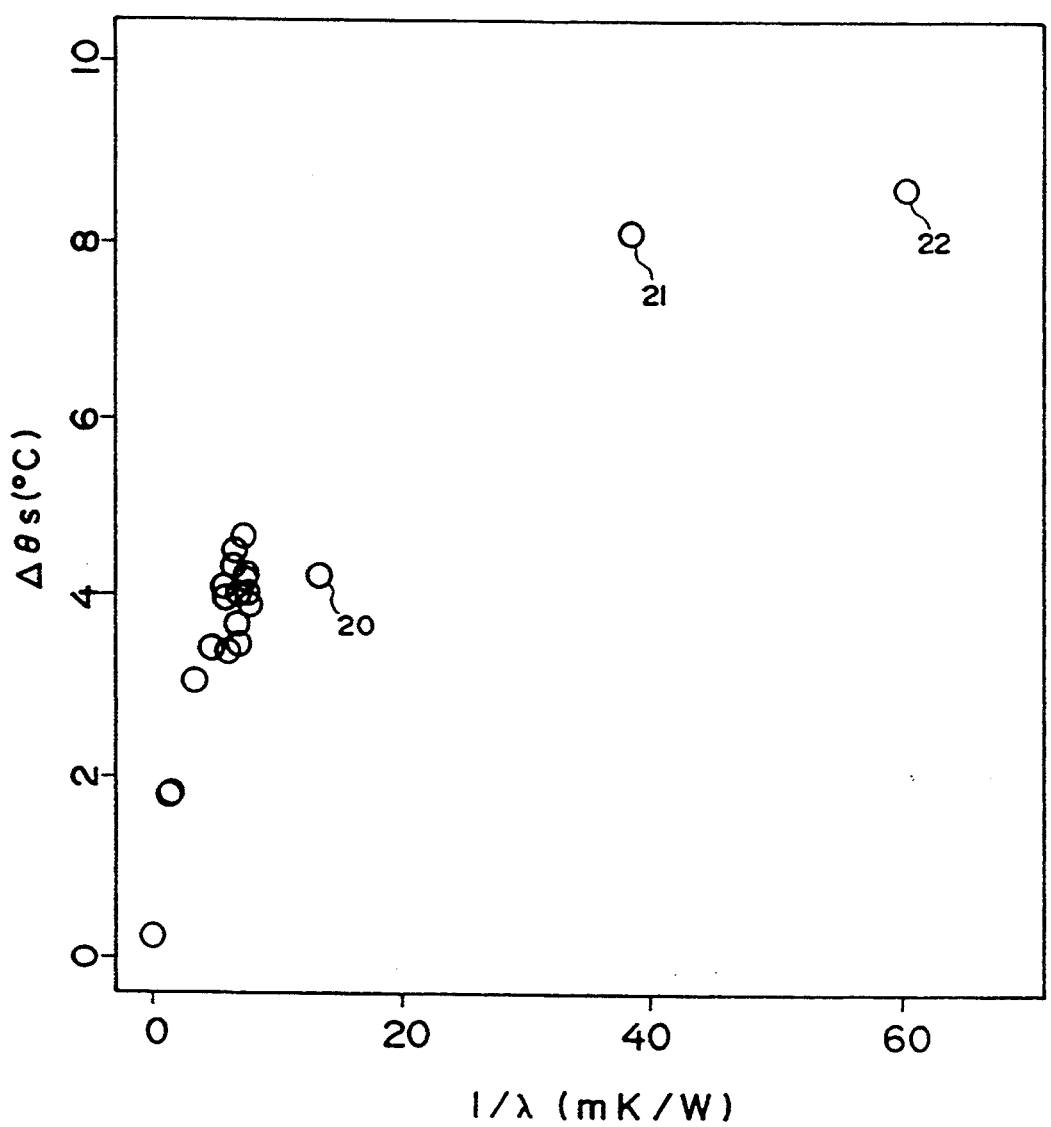

Generation of convection results in a convective heat transfer that adversely affects measurement of thermal conductivity and, in consequence, there occurs scattering in the correlation between the differential temperature $\Delta\theta_S$ and the thermal conductivity λ, as seen from FIGS. 10 and 11. Such scattering allows generation of a convective heat transfer to be detected.

FIG. 10 relates to the measurement made on liquids while FIG. 11 relates to the measurement made on gases.

Figure 12:
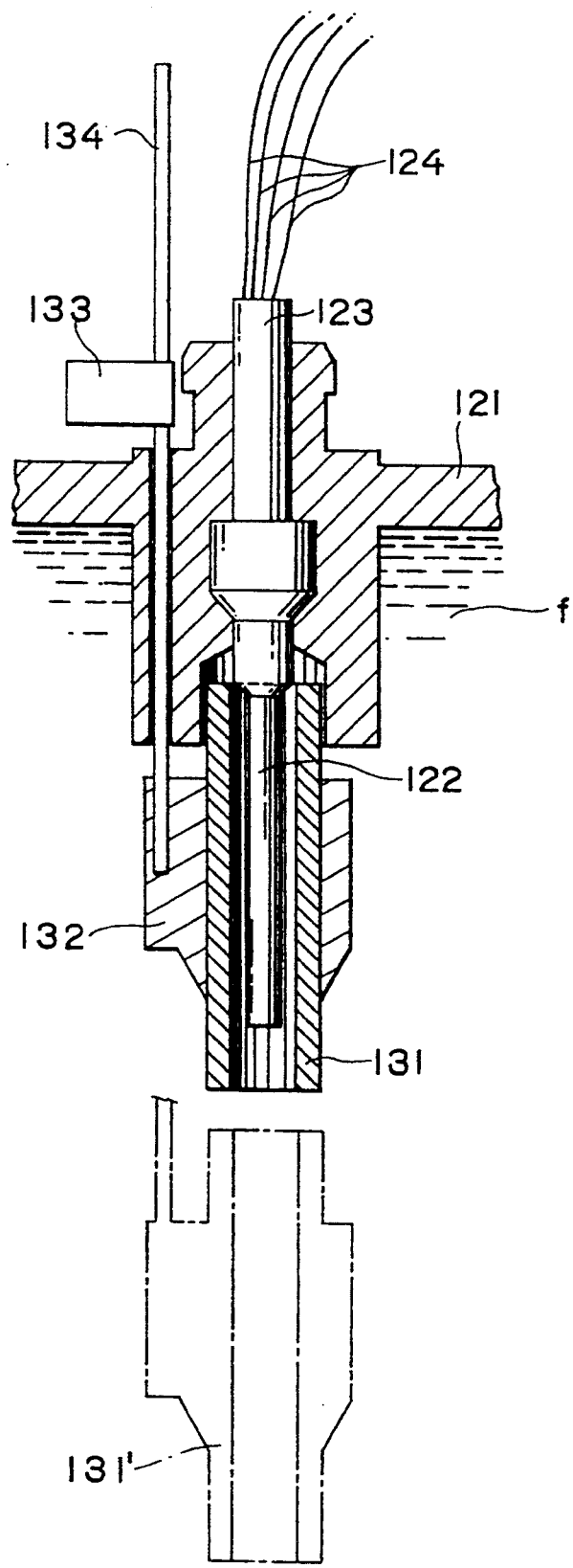
FIG. 12 is a sectional view, taken in an axial direction, showing second embodiment of the cylindrical heating sensor used for the method of the invention.

FIG. 12 is a sectional view showing a second embodiment of the inventive apparatus adapted to be used for the method of the invention. There is provided within a fluid tank 121 containing the fluid f being measured a cylindrical heating sensor 122 which preferably extends in vertical direction just as in the first embodiment.

The heating sensor 122 has its base end 123 projecting externally of the fluid tank 121 and four lead wires 124 for four-terminal measurement are connected to said base end 123.

Construction of this heating sensor 122 is substantially same as that in the embodiment as shown by FIG. 2.

As will be apparent from FIG. 12, there is provided a cylindrical hollow spacer 131 around the heating sensor 122 so as to maintain a predetermined clearance therebetween. Lower end of a rod 134 adapted to be vertically moved by drive means 133 is coupled to a support member 132 for the cylindrical hollow spacer 131 so that, when the spacer 131 has reached a position as shown by single dot chain line 131' under operation of said drive means 133, the fluid f may freely flow around the heating sensor 122.

Instead of such arrangement that the spacer is vertically movable, there may be provided around the heating sensor 122 a stationary spacer so that a predetermined clearance be maintained therebetween and the fluid f be introduced into this clearance under a pressure provided by vane, pump, piston or the like (not shown).

Figure 13:
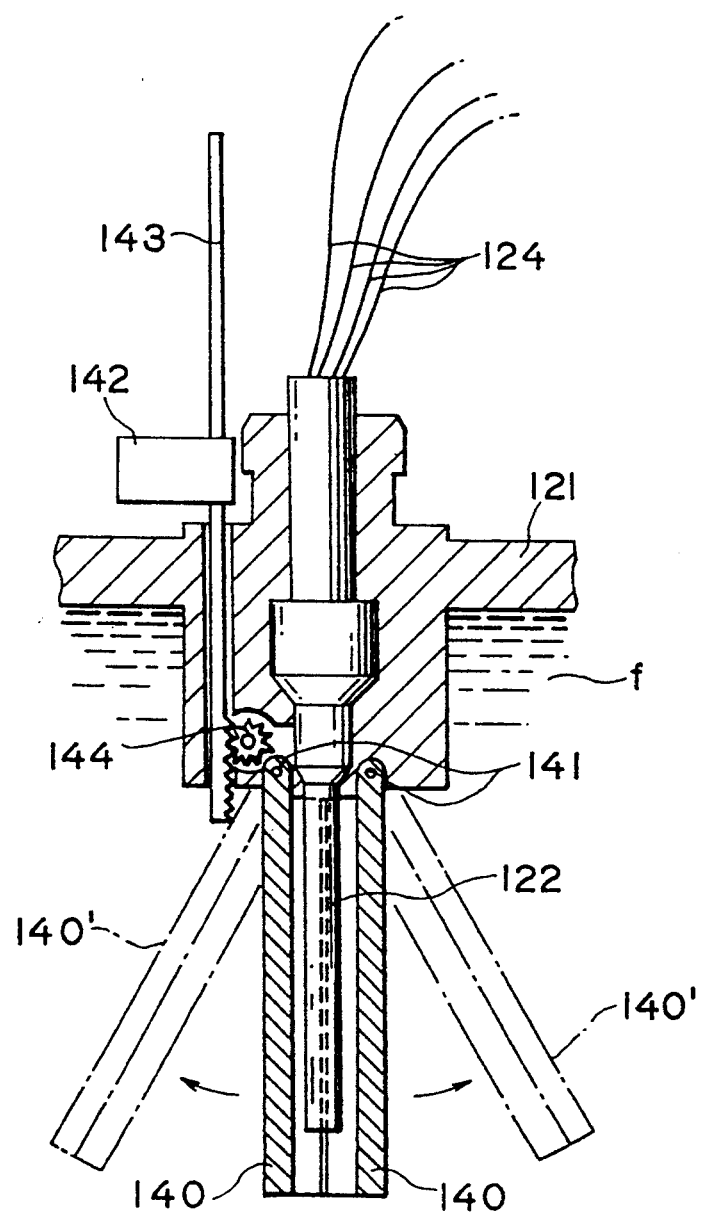
FIG. 13 is a sectional view, taken in an axial direction, showing third embodiment of the cylindrical heating sensor used for the method of the invention.

FIG. 13 is a sectional view showing a third embodiment of the inventive apparatus adapted to be used for the method of the invention. The cylindrical heating sensor 122 is surrounded by a two-piece spacer 140 comprising two halves of a cylinder. These cylinder halves 140 are rotatable around respective pivots 141 on which their upper ends are connected and are rotated by a gear 144 away from each other as a rod 143 is moved downward by drive means 142. When the respective halves 140 have reached positions 140' as shown by single dot chain lines, the fluid f may freely flow around the heating sensor 122.

Figure 14:
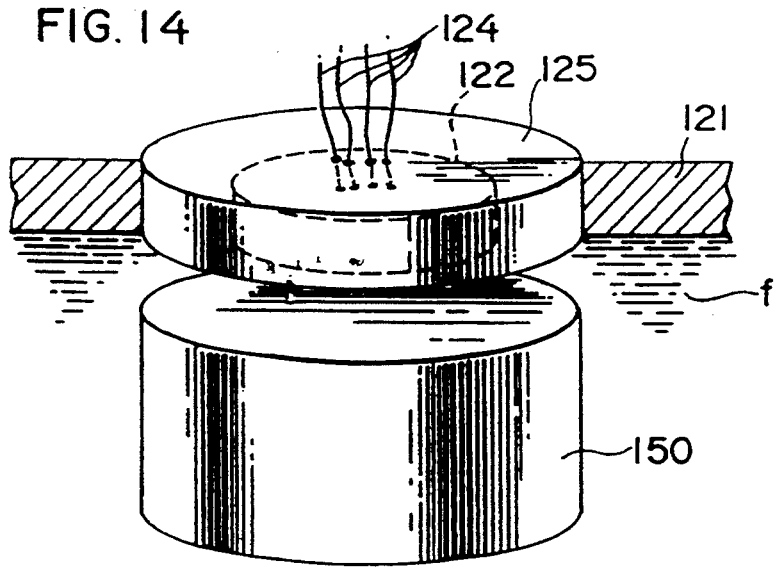
FIG. 14 is a sectional view, taken in an axial direction, showing a planar heating sensor as fourth embodiment of the heating sensor used for the method of the invention.

FIG. 14 schematically illustrates a fourth embodiment of the inventive apparatus adapted to be used for the method of the invention, in which the heating sensor 122 has a planar heating surface.

There is provided a spacer 150, which is correspondingly planar so as to define a predetermined clearance with respect to the heating sensor 122. The heating sensor 122 is covered with an insulator 125 except where the heating surface contacts the fluid.

With the heating sensors used in the second through fourth embodiments, it is possible in the same manner as with the heating sensor used in the first embodiment to measure a thermal conductivity of the fluid f. More specifically, temperatures of the fluid f and the heating sensor itself are measured, then a differential temperature therebetween is determined, and a thermal conductivity of the fluid f is obtained on the basis of a previously established relationship between the differential temperature and the thermal conductivity. It is also possible, with the spacer being largely spaced from the heating sensor, to determine a thermal conductivity of the fluid f in non steady state mode utilizing a gradient exhibited by a rectilinear portion of the differential temperature characterizing line as a function of log of a time elapsing after energization has been started.

As in the first embodiment, the optimal clearance defined between the heating sensor 122 and the hollow spacer 131 largely depends on factors such as a diameter of the heating sensor 122 or a viscosity of the fluid being measured. Particularly when the fluid has a relatively high viscosity, the clearance may be dimensioned correspondingly large since such high viscosity makes generation of a convection difficult. It is preferable to select the procedure of measurement depending on a viscosity of the fluid being measured for the apparatus adapted to be used both in steady state mode and non steady state mode. Dimensioning of the clearance is easier for the heating sensor 122 having a planar heating surface as shown by FIG. 14 than for the cylindrical heating sensor because the former allows the clearance to be dimensioned relatively large. Accordingly, the previously dimensioned clearance for the case of the cylindrical heating sensor is applicable to the heating sensor having the planar heating surface.

Figure 15:
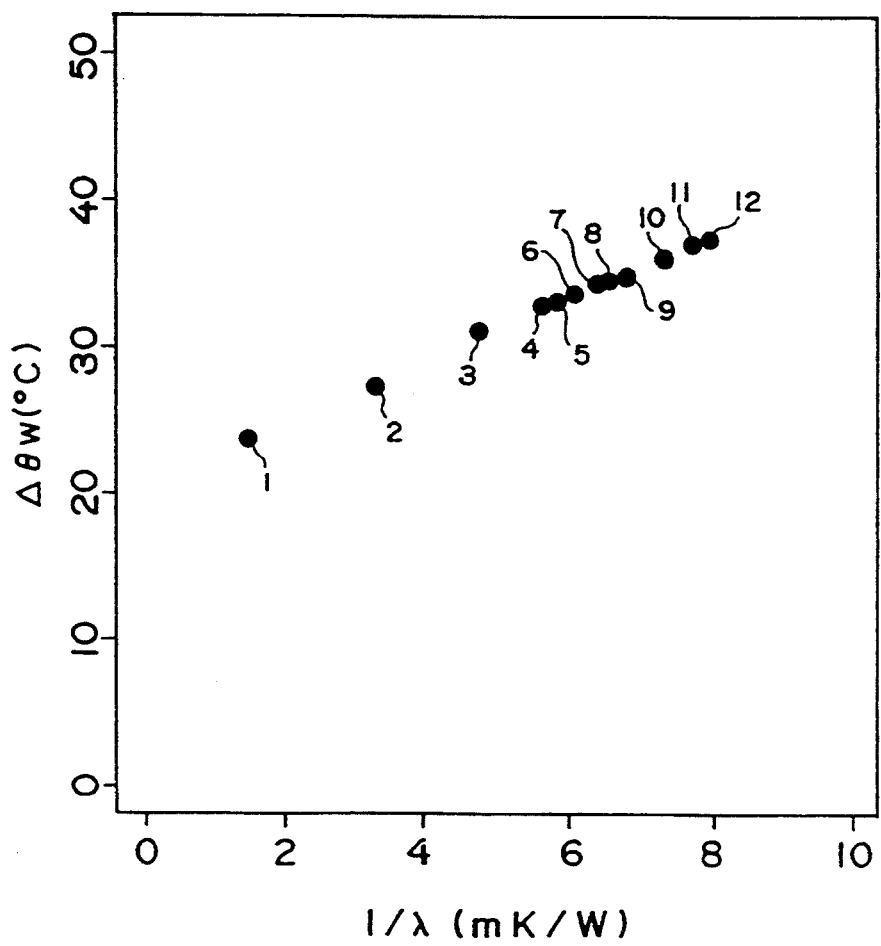
FIG. 15 is a graphic diagram plotting temperature difference $\Delta\theta_W$ versus reciprocal of $\lambda$ ($\lambda$: thermal conductivity).

FIG. 15 and Table 3 exemplarily show index values $\Delta\theta_W$ versus the reciprocal λ (λ: thermal conductivity).

TABLE 3

| FLUID SAMPLE | Thermal CONDUCTIVITY (W/mK) (LITERATURE-REPORTED VALUE 25° C.) | $\Delta\theta_W$ EXPERIMENTAL (°C.) | $\Delta\theta_S$ BASED ON NUMERIC (°C.) | Thermal CONDUCTIVITY OBTAINED BY REGRESSION | Thermal CONDUCTIVITY OBTAINED BY NON STEADY STATE MODE |
|---|---|---|---|---|---|
| water | 0.610 | 23.61 | 4.188 | 0.599 | 0.62 |
| glycerine | 0.287 | 27.25 | 8.350 | 0.300 | 0.22 |
| methanol | 0.203 | 31.12 | 11.155 | 0.195 | 0.21 |
| aniline | 0.172 | 32.72 | 13.078 | 0.170 | 0.17 |
| ethanol | 0.167 | 33.17 | 13.313 | 0.164 | 0.17 |
| acetone | 0.160 | 33.63 | 13.227 | 0.158 | 0.16 |
| n-butanol | 0.152 | 34.33 | 14.527 | 0.150 | 0.16 |
| **helium | 0.149 | 34.40 | 14.815 | 0.149 | 0.16 |
| benzene | 0.143 | 34.92 | 14.981 | 0.144 | 0.15 |
| pentanol | 0.134 | 35.90 | 15.900 | 0.134 | 0.14 |
| n-heptane | 0.130 | 37.07 | 16.238 | 0.130 | 0.14 |
| n-hexane | 0.123 | 37.38 | 16.506 | 0.123 | 0.13 |

TABLE 3-continued

| FLUID SAMPLE | Thermal CONDUCTIVITY (W/mK) (LITERATURE-REPORTED VALUE 25° C.) | $\Delta \theta_W$ EXPERIMENTAL (°C.) | $\Delta \theta_S$ BASED ON NUMERIC (°C.) | Thermal CONDUCTIVITY OBTAINED BY REGRESSION | Thermal CONDUCTIVITY OBTAINED BY NON STEADY STATE MODE |
|---|---|---|---|---|---|
| | | | *** | | |

**gas

***$\lambda \approx \dfrac{2}{(\Delta\theta_W - 20)}$

A series of experiment are made under the condition: the heating sensor having a diameter of 1 mm; the clearance of 0.25 mm; and the heating value of 2 W/m.

It should be understood that, when a thermal conductivity of a stationary fluid is measured with the cylindrical heating sensor 122 as shown by FIG. 12 or 13, a thermal conduction within a multi-cylinder modeled on the basis of the equation (1) may be utilized.

In equation (1), Q, L, $r_2$ and $r_1$ are practically real numeric values and therefore a liner relationship can be presupposed between the reciprocal $1/\lambda$ of thermal conductivity and the index value (differential temperature $\Delta\theta_W$.) As will be appreciated, FIG. 15 and Table 3 do not conflict with such presupposition.

With the instant embodiment, a regression formula was obtained by numerically processing the data as shown by FIG. 15 as follows;

$$\lambda \approx 2/(\Delta\theta_W - 20)$$

As will be apparent from the foregoing description, the essential feature of the invention is that a heat conductivity $\lambda$ of fluid can be measured by determination of differential temperature. $\lambda$ makes it possible to identify the kind of fluid when various kinds of fluid are intermittently introduced into the cylindrical pipe. This feature also allows a change in concentration to be detected as a change in thermal conductivity and to control a flow based on a degree of such change in a production line.

While the invention has been particularly shown and described with reference to preferred embodiments thereof, it will be understood by those skilled in the art that various changes in form and details can be made therein without departing from the spirit and scope of the invention.

What is claimed is:

1. Method for measuring a thermal conductivity of a fluid comprising the steps of:
   disposing a heating sensor, having heating means for heating the heating sensor and measuring means for measuring the temperature of the heating sensor, in a container for the fluid and heating the heating sensor with the heating means at a steady state of heating and measuring the temperature of the heating sensor with the measuring means, and wherein a clearance between an inner wall of the container and an outer wall of the heating sensor is dimensioned so that the measurement of thermal conductivity is free from any influence of a convective heat transfer due to a convection caused by heat generation from the heating sensor;
   measuring a temperature of the fluid;
   determining a differential temperature between the measured temperature of the heating sensor and the measured temperature of the fluid; and
   determining the thermal conductivity of the fluid on a basis of a correlation between the differential temperature and the thermal conductivity.

2. Method for measuring the thermal conductivity of a fluid as recited in claim 1, further including the steps of:
   determining a plurality of differential temperatures with a plurality of different clearances;
   determining a coefficient of the correlation between the thermal conductivity and the differential temperatures; and
   determining the optimum clearance between the inner wall of the container and the outer wall of the heating sensor based on the coefficient of correlation.

3. Method for measuring the thermal conductivity of a fluid as recited in claim 2, wherein said coefficient of correlation is at least 0.995.

4. Method for measuring the thermal conductivity of a fluid as recited in claim 1, wherein the clearance is dimensioned to be less than 0.8 mm in association with said heating sensor having a diameter less than 3.5 mm.

5. Method for measuring the thermal conductivity of a fluid as recited in claim 1, wherein the clearance between the inner wall of the container and the outer wall of the heating sensor is maintained by a spacer means, held at an appropriate distance from an outer surface of the heating sensor.

6. Method for measuring the thermal conductivity of a fluid as recited in claim 1, wherein the temperature of the heating sensor is a surface temperature of the heating sensor or an average temperature of a heating element contained in the heating sensor.

7. Method for measuring the thermal conductivity of a fluid as recited in claim 1, wherein the temperature of the fluid is controlled by a thermostatic means.

8. Method for measuring the thermal conductivity of a fluid as recited in claim 1, wherein
   the heating sensor is also adapted to measure the temperature of the fluid in the container; and
   wherein the correlation is in part established between a heating value of the heating sensor when heat generation thereof is so-controlled as to maintain said differential temperature at a constant value.

9. An apparatus for measuring a thermal conductivity of a fluid, comprising:
   a heating sensor having heating means for heating the heating sensor with the heating means at a steady state of heating and measuring means for measuring the temperature of the heating sensor and being disposable in a container for the fluid wherein a clearance between an inner wall of the container and an outer wall of the heating sensor is dimensioned so that the measurement of thermal conductivity is free from any influence of convective heat transfer due to convection caused by heat generation from the heating sensor;

means for measuring the temperature of the fluid;

means for determining a differential temperature between the measured temperature of the fluid and the heating sensor; and means for determining the thermal conductivity of the fluid on a basis of a correlation between the differential temperature and the thermal conductivity.

10. Apparatus for measuring the thermal conductivity of a fluid as recited in claim 9, wherein the heating sensor is disposed within a measuring pipe arranged to be closed such that the fluid being measured cannot flow therein for a predetermined period, and wherein thermostatic means enclose or partially cover the measuring pipe.

11. Apparatus for measuring a thermal conductivity of a fluid as recited in claim 9, wherein a spacer is adapted to maintain the clearance.

* * * * *